(12) United States Patent
Karasek et al.

(10) Patent No.: US 12,427,889 B2
(45) Date of Patent: Sep. 30, 2025

(54) METHOD OF SAFELY CONTROLLING COMPACTION MACHINE AND COMPACTION MACHINE FOR IMPLEMENTING THIS METHOD

(71) Applicant: AMMANN SCHWEIZ AG, Langenthal (CH)

(72) Inventors: Tomas Karasek, Bolehost (CZ); Lubos Fiala, Nebusice (CZ); Jan Svoboda, Jilovice (CZ); Stepan Valek, Nové Mesto nad Metuji (CZ)

(73) Assignee: AMMANN SCHWEIZ AG, Langenthal (CH)

( * ) Notice: Subject to any disclaimer, the term of this patent is extended or adjusted under 35 U.S.C. 154(b) by 182 days.

(21) Appl. No.: 18/263,631

(22) PCT Filed: Feb. 24, 2022

(86) PCT No.: PCT/EP2022/025062
§ 371 (c)(1),
(2) Date: Jul. 31, 2023

(87) PCT Pub. No.: WO2022/184316
PCT Pub. Date: Sep. 9, 2022

(65) Prior Publication Data
US 2024/0083299 A1 Mar. 14, 2024

(30) Foreign Application Priority Data
Mar. 3, 2021 (CZ) .................... CZ2021-98

(51) Int. Cl.
*B60L 58/13* (2019.01)
*B60L 50/60* (2019.01)
(Continued)

(52) U.S. Cl.
CPC ............ *B60L 58/13* (2019.02); *B60L 50/60* (2019.02); *B60Q 9/00* (2013.01); *E01C 19/282* (2013.01);
(Continued)

(58) Field of Classification Search
CPC .. B60L 58/13; B60L 50/60; B60L 1/00; B60L 7/10; B60L 2200/40; B60L 2260/162; B60Q 9/00; E01C 19/282
See application file for complete search history.

(56) References Cited

U.S. PATENT DOCUMENTS 8,585,317 B1 * 11/2013 Sina .................. E02D 3/074
404/117
12,139,876 B2 * 11/2024 Ivanov .................. H02K 7/063
(Continued)

FOREIGN PATENT DOCUMENTS

DE 102010006993 A1 8/2011
EP 0917978 A2 5/1999
(Continued)

OTHER PUBLICATIONS

Industrial Property Office of the Czech Republic Search Report mailed Aug. 30, 2021 in corresponding Czech Republic Application No. PV 2021-98.
(Continued)

*Primary Examiner* — Gertrude Arthur Jeanglaude
(74) *Attorney, Agent, or Firm* — Renner, Otto, Boisselle, & Sklar, LLP.

(57) ABSTRACT

A method of safely controlling a compaction machine, specifically a method of safely controlling a vibratory compaction machine includes at least one vibrating roller connected to at least one electric movement drive of the machine and at least one electric vibration drive, a central machine control unit, a battery system and a control unit of
(Continued)

Figure 1:
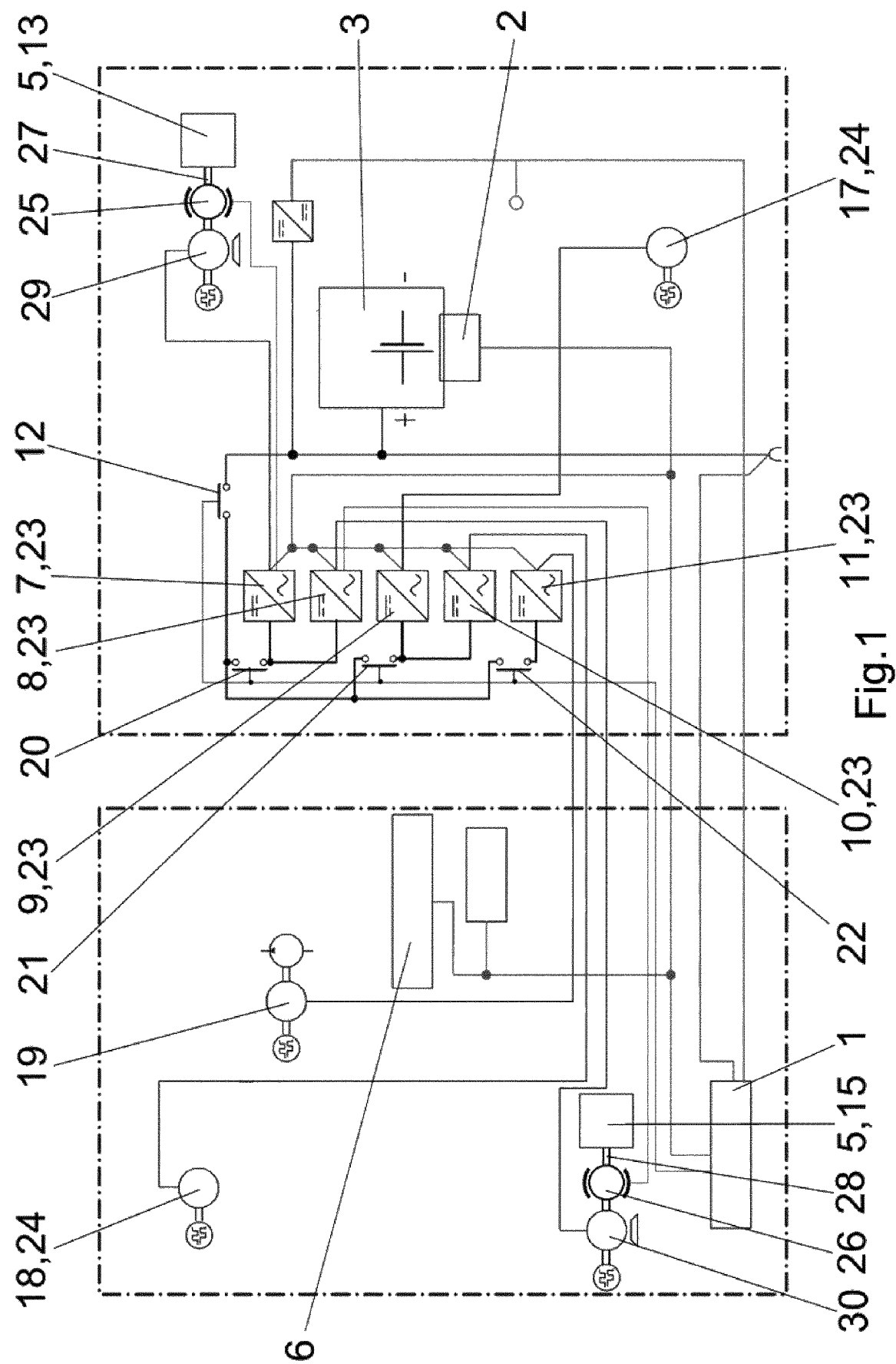

the battery system, according to which the central control unit of the machine overrides the control unit of the battery system. A compaction machine whose central control unit of the machine is data-connected to a control unit of the battery system which is hardwired to at least one control convertor of at least one electric drive of the machine.

19 Claims, 3 Drawing Sheets

(51) Int. Cl.
*B60Q 9/00* (2006.01)
*E01C 19/28* (2006.01)
*B60L 1/00* (2006.01)
*B60L 7/10* (2006.01)

(52) U.S. Cl.
CPC . *B60L 1/00* (2013.01); *B60L 7/10* (2013.01); *B60L 2200/40* (2013.01); *B60L 2260/162* (2013.01)

(56) References Cited

U.S. PATENT DOCUMENTS

2013/0006483 A1  1/2013  Ries
2022/0186453 A1*  6/2022  Steffen .................. E01C 19/26

FOREIGN PATENT DOCUMENTS

| EP | 1524367 A2 | 4/2005 |
| JP | 2015131559 A | 7/2015 |
| WO | 2015094023 A1 | 6/2015 |
| WO | 2019174897 A1 | 9/2019 |
| WO | 2020200509 A1 | 10/2020 |

OTHER PUBLICATIONS

International Search Report and Written Opinion Mailed Jun. 7, 2022 in corresponding international application No. PCT/EP2022/025062.

* cited by examiner

METHOD OF SAFELY CONTROLLING COMPACTION MACHINE AND COMPACTION MACHINE FOR IMPLEMENTING THIS METHOD

TECHNICAL FIELD

The invention relates to a method for safely controlling a compaction machine, specifically to a method for controlling a vibratory compaction machine comprising at least one vibrating roller connected to electric movement and vibration drives.

STATE OF THE ART

Currently, a number of design solutions for compaction earthmoving machines are known, which are used for compacting the subsoil and are used, for example, for compacting freshly laid asphalt, soil and other compact-able materials. These subsoil compaction machines always have at least one rotating roller which compacts the subsoil by passing it over it. To increase the effectiveness of compaction, the vibrating rollers are provided with a vibrating mechanism acting on the rotating roller.

As far as vibrating roller drives are concerned, hydraulic motors, driven by internal combustion engines but also by a central electric motor as a replacement for internal combustion engines, are most often used for both vibration drive and travel drive. The disadvantage of these drives is mainly their lower efficiency, design complexity and the resulting higher price. Another disadvantage is that they have a negative impact on the environment, both from the emissions of combustion engines aa well as possible leaks from hydraulic circuits.

The design solution of compaction machines with direct vibration and travel drive by means of electric motors and a central battery unit are also known from current technology. In these systems, for reasons of battery safety, the control battery system overrides the control unit of the entire machine. The disadvantage is that if the control system of the whole machine overrides the control battery system, then such a machine must have an independent working brake circuit, which significantly complicates the design of the compaction machine and makes it more expensive.

The use of electric motors for direct drive of machine travel and vibrations is known, for example, from patent documents WO2020200509A1, WO2019174897A1, US2013006483, EP1524367A2, WO2015094023A1 and DE102010006993A1.

From the above-mentioned current technology a number of disadvantages of the known designs are apparent, the most significant being the overall complexity and cost of designs containing electric drives, with the great disadvantage being the need to use an independent working brake circuit.

The object of the invention is the design of a compaction machine and setting a method for its safe control, which will allow a significant simplification of its construction, and thus a reduction in its price, all while maintaining all operational and safety standards.

PRINCIPLE OF THE INVENTION

The mentioned disadvantages are largely eliminated and the goal of the invention fulfilled by a method for safely controlling a compaction machine, specifically to a method for controlling a vibratory compaction machine comprising at least one vibrating roller connected to at least one electric drive and at least one electric vibration drive, a central machine control unit, a battery system, and a battery system control unit according to the invention, characterised by that the central control unit of the machine overrides the control unit of the battery system in such a way that at the moment when the electric drive of the machine acts as a service recuperation brake of the central control unit of the machine controls the control unit of the battery system so that when the battery system is charged to 100% of the set maximum charge limit, the battery system can be charged by the electric movement drive of the machine above this maximum charge limit of the battery system. The advantage of the invention is therefore the override of the control of the operation of the whole machine over the control of the operation of the battery system, which makes it possible to ensure the primary safety of the operator and the environment. This combines the functions of active safety and traction battery safety. All this allows the absence of an active independent working brake system and thus a significant simplification of the design of the entire machine and a significant reduction in its price.

It is to advantage if the battery system control unit is controlled by the machine's central control unit in such a way that, during normal machine operation, the battery system control unit maintains the battery system setting at a maximum charging limit lower than 100% of the maximum battery system charge value. The advantage is that this creates a reserve for possible excesses of 100% of the maximum charge value of the battery system, and thus protecting the batteries against damage.

It is to further advantage if the battery system control unit is controlled by the machine's central control unit in such a way that, during normal machine operation, the battery system control unit maintains the battery system setting at a maximum charging limit lower than 90% of the maximum battery system charge. The advantage being that a sufficient reserve is created for recharging the batteries when using the working recuperative brake.

It is also to advantage if the battery system control unit is controlled by the machine's central control unit in such a way that when the electric drive acts as the machine's recuperative working brake, the battery system control unit allows the battery system to be charged even when the battery system is charged to 100% of its maximum values. The advantage is that it is possible to safely stop and park the compaction machine the moment the battery system is 100% charged.

It is to further advantage if at the moment when the charging of the battery system reaches the set minimum or maximum charging limit, the machine control unit informs the battery system control unit of the machine's central control unit and the central control unit informs the machine operator via a peripheral control device thus allowing the central control unit of the machine to move it at a limited speed and limiting the use of all other machine functions. The advance is that the operator can adapt the operation of the machine to the approaching charging limit and stop and park in time, or avoid exceeding the charging limit.

It is also advantageous if the battery system control unit informs the central machine control unit when the battery system charge reaches the set minimum or maximum charging limit, and the central machine control unit informs the machine operator via the peripheral control device, the central machine control unit allowing movement of the machine at a limited speed and limits the use of all other machine functions. This is to advantage, for example, when the charge of the battery system reaches the minimum or maximum set charging limit, the battery control unit informs the central control unit of the machine, the central control unit of the machine switching off the safety contactor of the electric drive of cylinder vibration. Priority vibration shutdown is advantageous because the vibration drive consumes a relatively large amount of energy and is not necessary to stop the machine safely. In the same way, the sprinkler and possibly other functions that are not necessary for safely stopping the compaction machine are switched off.

Furthermore, it is to advantage if the central control unit of the machine puts the machine into a safe stationary state by switching off the contactors, which interrupts the power supply to the individual drives, thereby simultaneously interrupting the power supply to the control convertors and thus blocking at least one of the parking brakes. The advantage is that switching off the power supply not only interrupts the drives of the compaction machine, but also blocks the parking brake and thus secures the compaction machine in a stable position.

The above mentioned disadvantages are further largely eliminated and the goal of the invention fulfilled by a compaction machine, specifically the vibratory compaction machine according to the invention, characterised by that it comprises at least one vibrating roller connected to at least one electric drive and at least one electric vibration drive. a central machine control unit, a battery system and a battery system control unit, where the central machine control unit is data-connected to the battery system control unit which is hardwired to at least one control convertor of at least one electric machine drive, the control convertor of at least one electric machine movement drive is simultaneously hardwired to at least one electric machine movement drive, and data-connected to the central machine control unit, with the at least one electric machine movement drive being at the same time a working recuperation brake of the machine. The advantage is that due to the absence of an independent working brake, the overall design of the compaction machine is significantly simpler and thus the price of the machine is lower.

It to advantage if the battery system is hardwired to a charging contactor which is hardwired to at least the control convertor, with the charging contactor being data-connected to the central control unit of the machine. This ensures safe and easy control of the power supply to the drives.

It is also to advantage if the battery system is hardwired to the front cylinder drive electric control convertor which is hardwired to the front-roller electric movement drive, the front cylinder electric drive control convertor being data-connected to the machine's central control unit. The advantage is the possibility of simple and precise control of the movement of the front cylinder.

It is furthermore to advantage if the battery system is hardwired to a control convertor of the electric movement drive of the rear cylinder, which is hardwired to the electric movement drive of the rear cylinder, the control convertor of the electric drive of the rear cylinder being data-connected to the central control unit of the machine. The advantage is the possibility of simple and precise control of the movement of the rear cylinder.

Furthermore, it is also to advantage if the battery system is hardwired to a front vibration electric drive control convertor, which is hardwired to the front cylinder electric vibration drive, with the front roller electric vibration drive control convertor being data-connected to the machine central control unit. The advantage is the possibility of simple and precise control of the vibrations of the front cylinder.

To further advantage, the battery system is hardwired to the rear cylinder electric vibration drive control convertor, which is hardwired to the rear cylinder electric vibration drive, with the rear roller vibration electric drive control convertor being data-connected to the central machine control unit. The advantage is the possibility of simple and precise control of the vibrations of the rear cylinder.

It is also to advantage if the battery system is hardwired to an electric direction control convertor, which is hardwired to the electric direction control, with the electric direction control being data-connected to the central control unit of the machine. The advantage is the possibility of simple and precise control of the direction of movement of the entire compaction machine.

Furthermore, it is to advantage if, between the battery system and the control convertors of the electric roller drives is arranged a safety contactor for the electric movement drives, which is data-connected to the central control unit of the machine. The advantage is that, based on the command of the central control unit of the machine, it is possible to switch off the movement drives very quickly with the safety contactor of the electric movement drives, and thus to stop the entire machine safely.

It is also to advantage if, between the battery system and the control convertors of the electric roller vibration drives is arranged a safety contactor for the electric vibration drives, which is data-connected to the central control unit of the machine. The advantage is that, based on the command of the central control unit of the machine, it is possible to switch off the vibration drives very quickly with the safety contactor of the electric vibration drives.

It is further to advantage if, between the battery system and the control convertors of the electric direction control drive is arranged a safety contactor for the electric direction control drive, which is data-connected to the central control unit of the machine. The advantage is that, based on the command of the central control unit of the machine, it is possible to switch off the direction control drive very quickly with the safety contactor of the electric direction drive.

To advantage, the central control unit of the machine is further data-connected to the peripheral control device. This allows simple and fast transmission of information about the operation of the machine to its operator and at the same time fast and accurate control of the machine by the operator.

Furthermore, it is also to advantage if the central control unit is data-connected to an external computer device. The connection can be made via a data cable or wirelessly.

It is also to great advantage if at least one of the control convertors of the electric cylinder movement drives is hardwired to a parking brake arranged on the shaft of the electric drive, in order to mechanically block the movement of one of the rollers. The advantage is that the compaction machines can be securely fixed in the parking position.

The main advantage of the compaction machine and the method of safely controlling the compaction machine according to the invention is that due to the absence of an independent working brake it has a very simple design and therefore a a low price, all while maintaining all safety standards. Another great advantage is the emission-free operation, which will enable the operation of the compaction machine in urban areas and underground garages. Overriding of the central machine control unit by the battery system control unit allows the control unit of the battery system to safely control the individual functions of the machine with regard to the safety of the operator and the surroundings of the compaction machine, without reducing or limiting the life and safety of the traction battery. Another advantage is safe machine shutdown if the traction battery limits are reached.

OVERVIEW OF THE FIGURES

The invention will be further elucidated using drawings, in which

Figure 2:
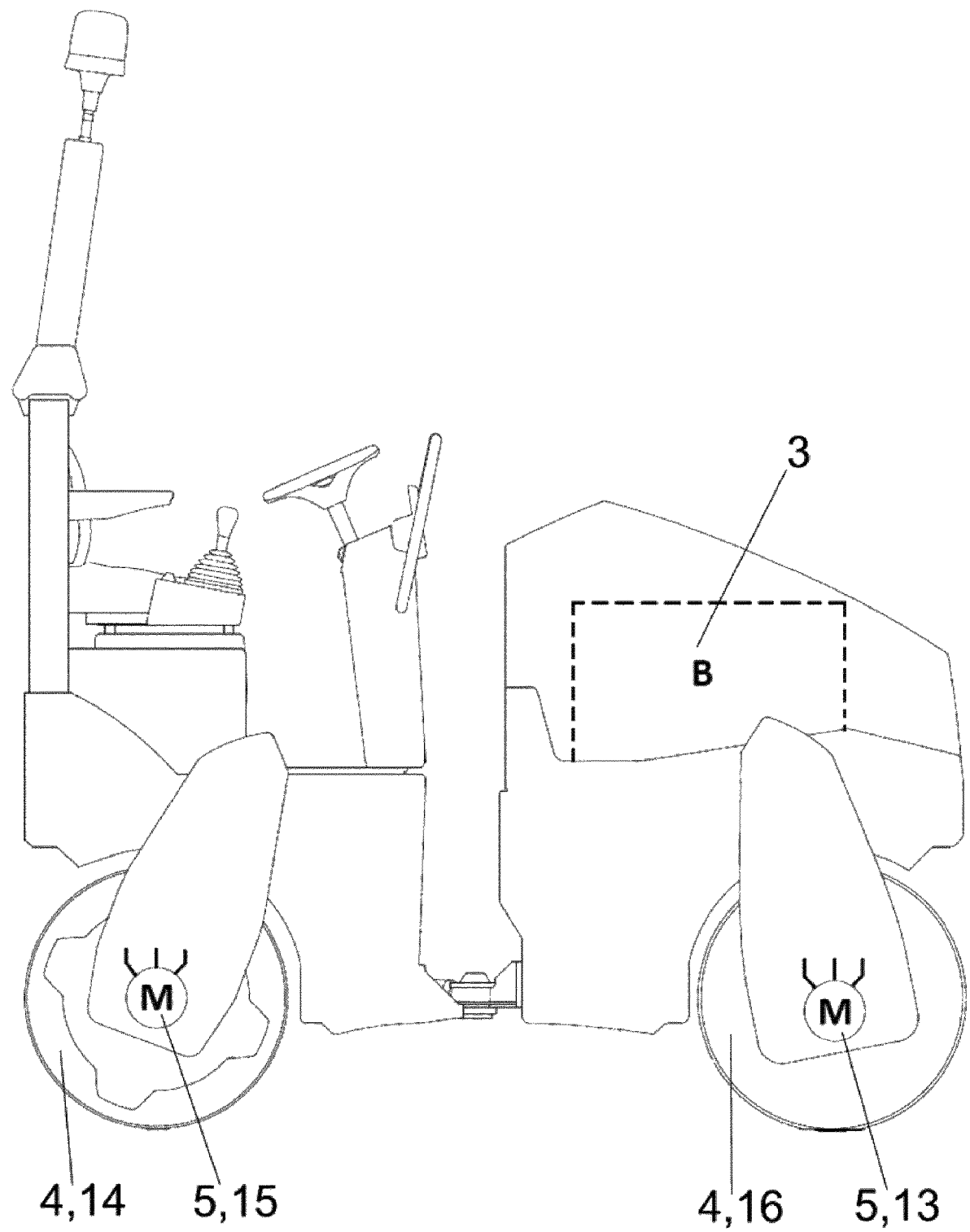
Figure 3:
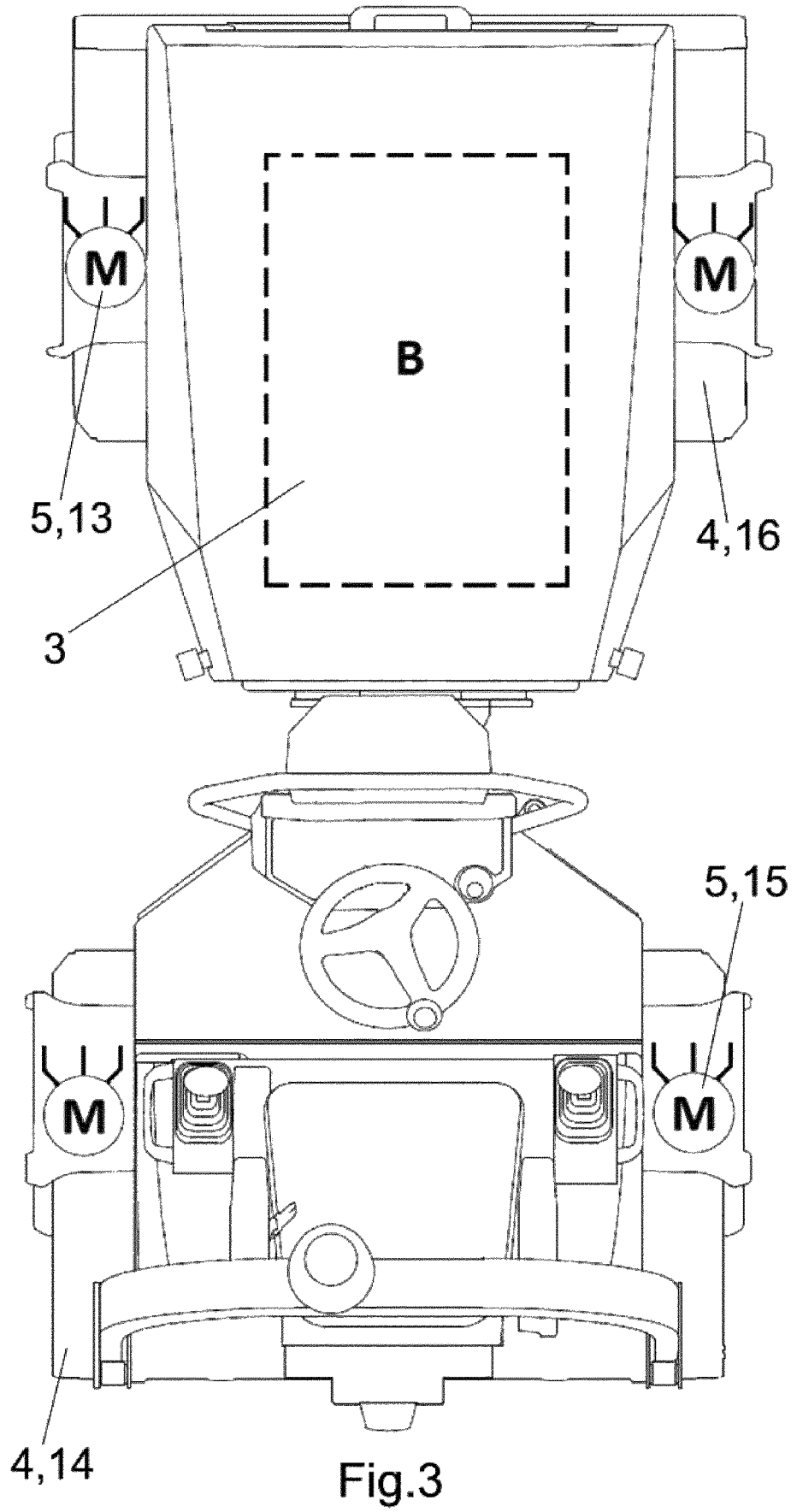

FIG. 1 shows the schematic hardwire and data connections of individual parts of a compaction machine, FIG. 2 shows a side view of a compaction machine with a schematically drawn location of a battery system and schematically drawn movement drives, and FIG. 3 shows an overhead view of a compaction machine with a schematically drawn location of the battery system and schematically drawn movement drives.

EXAMPLES OF THE PERFORMANCE OF THE INVENTION

The self-propelled vibratory compaction machine (FIG. 1, FIG. 2, FIG. 3) comprises two vibrating cylinders 4, namely a front vibrating cylinder 16 and a rear vibrating cylinder 14, which are connected to the electric movement drives 5 of the machine by an electric movement drive 13 of the front cylinder 16 and the electric movement drive 15 of the rear cylinder 14. The front vibrating roller 16 further comprises electric vibration drives 17, 24 and the rear vibrating cylinder 14 comprises electric vibration drives 18, 24. The compaction machine further comprises a central control unit 1 of the machine, a battery system 3 and a control unit 2 of the battery system 3.

The central control unit 1 of the machine is data-connected to the control unit 2 of the battery system 3, which is hardwired to the five control convertors 7, 8, 9, 10, 11, 23 of the electric drives 5, 19, 24 of the machine. The control convertors 7, 8, 9, 10, 11, 23 of the electric drives 5, 19, 24 of the machine are simultaneously hardwired to these electric drives 5, 19, 24. The control convertors 7, 8, 9, 10, 11, 23 of the electric drives 5, 19, 24 of the machine are simultaneously data-connected to the central control unit 1 of the machine.

Both electric drives 5, 13, 15 of the machine movement are at the same time the working recuperation brake of the machine.

The battery system 3 is hardwired to a charging contactor 12, which is hardwired to the control convertors 7, 8, 9, 10, 11, 23, with the charging contactor 12 being data-connected in analogue to the central control unit 1 of the machine.

The battery system 3 is hardwired to the control convertor 7, 23 of the electric movement drive 13 of the front cylinder 16, which is hardwired to the electric movement drive 13 of the front cylinder 16, with the control convertor 7, 23 of the electric movement drive 13 of the front cylinder 16 being data-connected to the central control unit 1 of the machine.

The battery system 3 is further hardwired to the control convertor 8, 23 of the electric movement drive 15 of the rear cylinder 14, which is hardwired to the electric movement drive 15 of the rear cylinder 14, the control convertor 8, 23 of the electric movement drive 15 of the rear cylinder 14 being data-connected with central control unit 1 of the machine.

The battery system 3 is hardwired to the control cylinder 9, 23 of the electric vibration drive 17 of the front cylinder 16, which is hardwired to the electric vibration drive 17 of the front cylinder 16, with the control convertors 9, 23 of the electric vibration drive 17 of the front cylinder 16 being data-connected to the central control unit 1 of the machine.

The battery system 3 is hardwired to the control convertor 10, 23 of the electric vibration drive 18 of the rear cylinder 14, which is hardwired to the electric vibration drive 18 of the rear cylinder 14, with the control convertors 10, 23 of the electric vibration drive 18 of the rear cylinder 14, being data-connected to central control unit 1 of the machine.

The battery system 3 is hardwired to the control convertors 11, 23 of the electric direction control drive 19, which is hardwired to the electric direction control drive 19, the control direction convertor 11, 23 of the electric direction control drive 19 being data-connected to the central control unit 1 of the machine.

Between the battery system 3 and the control convertors 7, 8 of the electric movement drives 13, 15 of the cylinders 14, 16, a safety contactor 20 of the electric movement drives 13,15 is arranged, which is data-connected to the central control unit 1 of the machine.

Between the battery system 3 and the control convertors 9, 10 of the electric vibration drives 17, 18 of the cylinders 14, 16, a safety contactor 21 of the electric vibration drives 17, 18 is arranged, which is data-connected to the central control unit 1 of the machine.

Between the battery system 3 and the control convertor 11 of the electric direction control drive 19, a safety contactor 22 of the electric direction control drive 19 is arranged, which is data-connected to the central control unit 1 of the machine.

The central control unit 1 of the machine is wirelessly connected to the peripheral control device 6.

The central control unit 1 is occasionally data-connected to an external computing device (not shown).

The control convertor 7 of the the electric movement drive 13 of the front cylinder 16, is hardwired to a parking brake 25 arranged on the shaft 27 between the electric movement drive 13 of the front cylinder 16 and the gearbox 29 to mechanically block the movement of the front cylinder 16. The control convertor 8 of the electric movement drive 15 of the rear cylinder 14 is hardwired to the parking brake 26 arranged on the shaft 28 between the electric movement drive 15 of the rear cylinder 14 and the gearbox 30, to mechanically block the movement of the rear cylinder 14. The parking brakes 25, 26 at the moment when the contactors 12, 20, 21, 22 switch off, mechanically block the movement of the cylinders 14, 16.

The battery system 3 is hardwired via a power supply to the central control unit 1 of the machine. At the same time, the battery system 3 is hardwired to an external charging device (not shown).

The control unit 2 of the battery system 3 is part of the battery system 3.

According to the method of safely controlling a self-propelled vibratory compaction machine, the central control unit 1 of the machine overrides the control unit 2 of the battery system 3 in such a way that at the moment when the electric movement drive 5 operates as a working recuperation brake of the machine, the central control unit 1 of the machine controls the control unit 2 of the battery system 3 in such a way that the control unit 2 of the battery system 3 allows, when the battery system 3 is charged to 100% of the value of the set maximum charging limit, the charging of the battery system 3 by the electric movement drive 5 of the machine above this maximum charging limit of the battery system 3.

The control unit 2 of the battery system 3 maintains, during normal operation of the machine, the setting of the battery system 3 at the maximum charging limit, the value of which is 98% of the maximum charge value of the battery system 3. Alternatively, taking into account the specific operating conditions of the compaction machine, the maximum charging limit can be set at values of 85 to 99% of the maximum charge value of the battery system 3.

The control unit 2 of the battery system 3 is controlled by the central control unit 1 of the machine in such a way that at the moment when the electric drive 5 acts as a working recuperation brake of the machine, the control unit 2 of the battery system 3 allows charging the battery system 3 even when the battery system 3 is charged to 100% of its maximum value.

As soon as the charge of the battery system 3 approaches the set maximum or minimum charging limit, the control unit 2 of the battery system 3 informs the central control unit 1 of the machine and the central control unit 1 of the machine informs the machine operator via the peripheral control device 6 and allows all functions of the machine to be used without restriction. The status marked "Warning to the operator" corresponds to this status in the attached table with setting examples.

As soon as the charge of the battery system 3 reaches the set minimum or maximum charging limit, the control unit 2 of the battery system 3 informs the central control unit 1 of the machine and the central control unit 1 of the machine informs the machine operator via the peripheral control device 6, and the central control unit 1 of the machine allows the machine to move at a limited speed and limits the use of all other machine functions. For example, the central control unit 1 of the machine switches off the safety contactor 21 of the electric vibration drive 24 of the cylinder 4. Furthermore, in the same way it is possible to switch off the sprinkling system (not shown). The status marked "Functionality limitation" corresponds to this state in the attached table with setting examples.

The central control unit 1 of the machine puts the machine into a safe stationary state by switching off the contactors 12, 20, 21, 22, which interrupts the power supply to the individual drives 13, 15, 17, 18, 19, which simultaneously interrupts supply of electrical energy to the control convertors 7, 8 and thus to block the parking brakes 25, 26. The state marked "Safe shutdown" corresponds to this state in the enclosed table with setting examples.

The minimum and maximum charging limits can be set with respect to the operating conditions of the machine, for example with respect to the local temperature or the battery condition, or with regard to the operating history at a given location, their variable value being controlled by the machine's central control unit 1. Or these limits can be set to be fixed.

EXAMPLES OF FIXED CHARGING LIMITS

Example 1

| Degrees of protection | Minimum battery capacity | Maximum battery capacity |
|---|---|---|
| Warning to the operator | 5% | 95% |
| Functional limitations | 2% | 98% |
| Safe shutdown | 1% | 100% |

Example 2

| Degrees of protection | Minimum battery capacity | Maximum battery capacity |
|---|---|---|
| Warning to the operator | 10% | 93% |
| Functional limitations | 5% | 95% |
| Safe shutdown | 3% | 98% |

Example 3

| Degrees of protection | Minimum battery capacity | Maximum battery capacity |
|---|---|---|
| Warning to the operator | 7% | 91% |
| Functional limitations | 3% | 93% |
| Safe shutdown | 1% | 95% |

Example 4

| Degrees of protection | Minimum battery capacity | Maximum battery capacity |
|---|---|---|
| Warning to the operator | 9% | 85% |
| Functional limitations | 4% | 88% |
| Safe shutdown | 2% | 90% |

Example 5

| Degrees of protection | Minimum battery capacity | Maximum battery capacity |
|---|---|---|
| Warning to the operator | 9% | 81% |
| Functional limitations | 7% | 83% |
| Safe shutdown | 5% | 85% |

INDUSTRIAL APPLICATION

A method of safely controlling a compaction machine and a compaction machine for implementing this method, according to the invention, can be used on construction compaction machines provided to the maximum extent possible with electric drives.

LIST OF REFERENCE MARKS

1 central machine control unit
2 control unit of the battery system
3 battery system
4 vibrating cylinder
5 electric movement drive
6 peripheral control device
7 electric drive control convertor of the front cylinder
8 electric drive control convertor of the rear cylinder
9 electric vibration drive control convertor of the front cylinder 10 electric vibration drive control convertor of the rear cylinder
11 direction control drive convertor
12 charging contactor
13 electric movement drive of the front cylinder
14 rear cylinder
15 electric movement drive of the rear cylinder
16 front cylinder
17 electric vibration drive of the front cylinder
18 electric vibration drive of the rear cylinder
19 direction control drive
20 safety contactor for electric movement drives
21 safety contactor for electric vibration drives
22 safety contactor for direction of movement
23 drive control convertor
24 electric vibration drive
25 front cylinder parking brake
26 rear cylinder parking brake
27 shaft I
28 shaft II
29 gearbox I
30 gearbox II

The invention claimed is:

1. A method of safely controlling a compaction machine, specifically the method of safely controlling a vibratory compaction machine comprising
at least one vibrating cylinder connected to at least one electric movement drive of the machine and at least one electric vibration drive,
a central machine control unit of the machine,
a battery system, and
a control unit of the battery system,
wherein the central control unit of the machine overrides the control unit of the battery system in such a way that at the moment when the electric movement drive of the machine acts as a working recuperative brake of the machine, the central control unit of the machine controls the control unit of the battery system in such a way that the control unit of the battery system allows, when the battery system is charged to 100% of the value of the set maximum charging limit, charging of the battery system by the electric movement drive above this maximum charging limit of the battery system, and
wherein the central control unit of the machine brings the machine into a safe stationary state by switching off the contactors, which interrupts the power supply to the individual drives, which at the same time interrupts the power supply to the control convertors, thereby blocking at least one of the parking brakes.

2. The method of safely controlling a compaction machine according to claim 1, wherein the control unit of the battery system is controlled by the central control unit of the machine so that the control unit of the battery system maintains, during normal operation of the machine, the setting of the battery system at the maximum charging limit, the value of which is lower than 100% of the maximum charge value of the battery system.

3. The method of safely controlling a compaction machine according to claim 1, wherein the control unit of the battery system is controlled by a central control unit of the machine in such a way that the control unit of the battery system maintains, during normal operation of the machine, the setting of the battery system at the maximum charging limit, the value of which is lower than 90% of the maximum charge value of the battery system.

4. The method of safely controlling a compaction machine according to claim 1, wherein the control unit of the battery system is controlled by a central control unit of the machine in such a way that at the moment when the electric drive acts as a working recuperation brake of the machine, the control unit of the battery system allows charging of the battery system even at the moment when the battery system is charged to 100% of its maximum values.

5. The method of safely controlling a compaction machine according to claim 1, wherein the moment the charging of the battery system approaches the set charging limit, the control unit of the battery system informs the central control unit of the machine, with the central control unit of the machine informing, via the peripheral control device, the machine operator and enabling the use of all machine functions without restriction.

6. The method of safely controlling a compaction machine according to claim 1, wherein at the moment when the charging of the battery system reaches the set charging limit, the control unit of the battery system informs the central control unit of the machine, with the central control unit of the machine informing, via the peripheral control device, the machine operator and allowing the machine to move at a limited speed and restricting the use of all other machine functions.

7. The method of safely controlling a compaction machine, according to claim 6, wherein at the moment when the charging of the battery system reaches the set charging limit, the control unit of the battery system informs the central control unit of the machine, with the central control unit switching off the safety contactor of the electric vibration drive of the cylinder.

8. A compaction machine, in particular a vibratory compaction machine for implementing the method of safely controlling a compaction machine according to claim 1, wherein it comprises at least one vibrating cylinder connected with at least one electric movement drive of the machine and at least one electric vibration drive, a central control unit of the machine, a battery system and a control unit of the battery system, with the central control unit of the machine being data-connected to the control unit of the battery system, which is hardwired to at least one control convertor of at least one electric drive of the machine, and the control convertor of at least one electric movement drive of the machine is simultaneously hardwired to at least one electric movement drive of the machine, and data-connected to the central control unit of the machine, and at least one electric movement drive of the machine being at the same time the working recuperative brake of the machine, and
wherein the battery system is hardwired to a charging contactor which is hardwired to at least one control convertor, with the charging contactor being data-connected to the central control unit of the machine.

9. The compaction machine according to claim 8, wherein the battery system is hardwired to the control convertor of the electric movement drive of the front cylinder, which is hardwired to the electric movement drive of the front cylinder, the control convertor of the electric movement drive of the front cylinder being data-connected to the central control unit of the machine.

10. The compaction machine according to claim 8, wherein the battery system is hardwired to the control convertor of the electric movement drive of the rear cylinder, which is hardwired to the electric movement drive of the rear cylinder, the control convertor of the electric movement drive of the rear cylinder being data-connected to the central control unit of the machine.

11. The compaction machine according to claim 8, wherein the battery system is hardwired to the control convertor of the electric vibration drive of the front cylinder, which is hardwired to the electric vibration drive of the front cylinder, the control convertor of the electric vibration drive of the front cylinder being data-connected to the central control unit of the machine.

12. The compaction machine according to claim 8, wherein the battery system is hardwired to the control convertor of the electric vibration drive of the rear cylinder, which is hardwired to the electric vibration drive of the rear cylinder, the control convertor of the electric vibration drive of the rear cylinder being data-connected to the central control unit of the machine.

13. The compaction machine according to claim 8, wherein the battery system is hardwired to the control convertor of the electric direction control drive which is in hardwired to the electric direction control drive, the control convertor of the electric direction control drive being data-connected to the central control unit of the machine.

14. The compaction machine according to claim 8, wherein between the battery system and the control convertors of the electric movement drives of the rollers there is arranged a safety contactor of the electric movement drives, which is data-connected to the central control unit of the machine.

15. The compaction machine according to claim 8, wherein between the battery system and the control convertors of the electric vibration drives of the rollers, is arranged a safety contactor of the electric vibration drives, which is data-connected to the central control unit of the machine.

16. The compaction machine according to claim 8, wherein between the battery system and the control convertor of the electric direction control drive is arranged a safety contactor of the electric direction control drive, which is data-connected to the central control unit of the machine.

17. The compaction machine according to claim 8, wherein the central control unit of the machine is data-connected to the peripheral control device.

18. The compaction machine according to claim 8, wherein the central control unit of the machine is data-connected to an external computer device.

19. The compaction machine according to claim 8, wherein at least one of the control convertors of the electric movement drives of the cylinders is hardwired to a parking brake arranged on the shaft of the electric drive, to mechanically block the movement of one of the cylinders.

* * * * *